US012774923B2

(12) United States Patent
Okuda et al.

(10) Patent No.: US 12,774,923 B2
(45) Date of Patent: Oct. 27, 2026

(54) MONITORING SYSTEM AND MONITORING METHOD

(71) Applicant: Mitsubishi Electric Corporation, Tokyo (JP)

(72) Inventors: Satoshi Okuda, Tokyo (JP); Masaharu Hattori, Tokyo (JP); Yasuki Aihara, Tokyo (JP); Takashi Takenaga, Tokyo (JP); Kazuya Sato, Tokyo (JP); Yasuaki Susumu, Tokyo (JP); Kenichiro Chomei, Tokyo (JP)

(73) Assignee: Mitsubishi Electric Corporation, Tokyo (JP)

( * ) Notice: Subject to any disclaimer, the term of this patent is extended or adjusted under 35 U.S.C. 154(b) by 318 days.

(21) Appl. No.: 18/556,576

(22) PCT Filed: Sep. 15, 2021

(86) PCT No.: PCT/JP2021/033969
§ 371 (c)(1),
(2) Date: Oct. 20, 2023

(87) PCT Pub. No.: WO2023/042310
PCT Pub. Date: Mar. 23, 2023

(65) Prior Publication Data

US 2024/0192057 A1 Jun. 13, 2024

(51) Int. Cl.
*G06V 10/25* (2022.01)
*A61B 5/01* (2006.01)
(Continued)

(52) U.S. Cl.
CPC ............ *G01J 5/0025* (2013.01); *A61B 5/015* (2013.01); *A61B 5/1117* (2013.01);
(Continued)

(58) Field of Classification Search
CPC .................. G01J 5/0025; G01J 5/0859; G01J 2005/0077; G06V 10/25; G06V 20/52;
(Continued)

(56) References Cited

U.S. PATENT DOCUMENTS 10,553,099 B2 2/2020 Ikeda et al.
2017/0132473 A1* 5/2017 Okada .................... G06V 20/52
(Continued)

FOREIGN PATENT DOCUMENTS

CN 111052194 A * 4/2020 ......... G08B 21/0476
JP 2008-92538 A 4/2008
(Continued)

OTHER PUBLICATIONS

Computer translation of KR_20200134702_A (Year: 2025).*
(Continued)

*Primary Examiner* — Randy W Gibson
(74) *Attorney, Agent, or Firm* — Studebaker Brackett PLLC

(57) ABSTRACT

A thermal image acquisitor (3) is attached to a wall (4) or a ceiling (5) on a side of a head of a care recipient (1) in a case where the care recipient lies on a bed (2), and captures an image of the bed and its surroundings from diagonally above to acquire a thermal image. Reference setting circuitry (12) sets two reference lines (8,9) respectively corresponding to a left end and a right end of the bed in the thermal image, and a reference height (10) for determining sitting-up of the care recipient. Heat source detection circuitry (13) detects a mass (11) of a heat source in the thermal image. State determination circuitry (14) determines a state of the care recipient from a positional relationship between a safe area (15) enclosed with the reference lines and the reference height and the mass of the heat source.

18 Claims, 9 Drawing Sheets

(51) Int. Cl.

| | |
|---|---|
| ***A61B 5/11*** | (2006.01) |
| ***G01J 5/00*** | (2022.01) |
| ***G01J 5/08*** | (2022.01) |
| ***G06T 7/00*** | (2017.01) |
| ***G06V 20/52*** | (2022.01) |
| ***G06V 40/10*** | (2022.01) |

(52) U.S. Cl.
CPC ........... *A61B 5/1128* (2013.01); *G01J 5/0859* (2013.01); *G06T 7/0014* (2013.01); *G06V 10/25* (2022.01); *G06V 20/52* (2022.01); *G06V 40/103* (2022.01); *G01J 2005/0077* (2013.01); *G06T 2207/10048* (2013.01); *G06T 2207/30196* (2013.01); *G06T 2207/30232* (2013.01); *G06V 2201/03* (2022.01)

(58) Field of Classification Search
CPC ............... G06V 40/103; G06V 7/0014; G06V 2201/03; A61B 5/015; A61B 5/1117; A61B 5/1128; A61B 5/0859; G06T 2207/10048; G06T 2207/30196; G06T 2207/30232
See application file for complete search history.

(56) References Cited

U.S. PATENT DOCUMENTS

| | | | | |
|---|---|---|---|---|
| 2019/0043336 | A1 | 2/2019 | Ikeda et al. | |
| 2019/0090786 | A1* | 3/2019 | Kim | A61B 5/1117 |
| 2020/0103286 | A1 | 4/2020 | Ikeda et al. | |
| 2020/0349382 | A1* | 11/2020 | Chen | G06T 7/246 |

FOREIGN PATENT DOCUMENTS

| | | | | |
|---|---|---|---|---|
| JP | 2019-204366 | A | 11/2019 | |
| JP | 2020-057351 | A | 4/2020 | |
| JP | 6828703 | B2 | 2/2021 | |
| KR | 20200134702 | A * | 12/2020 | A61B 5/0002 |

OTHER PUBLICATIONS

Computer translation of CN_111052194_A (Year: 2025).*
International Search Report issued in PCT/JP2021/033969; mailed Nov. 30, 2021.
An Office Action; mailed by the China National Intellectual Property Administration of the People's Republic of China on Apr. 30, 2026, which corresponds to Chinese Patent Application No. 202180102236.4 and is related to U.S. Appl. No. 18/556,576.

* cited by examiner

MONITORING SYSTEM AND MONITORING METHOD

FIELD

The present disclosure relates to a monitoring system and a monitoring method using an infrared camera.

BACKGROUND

In hospitals or nursing homes, there is a possibility that if a care recipient such as an elderly person falls from a bed while sleeping, it may lead to a serious injury. It is therefore desired to prevent or promptly detect a fall accident. Thus, in hospitals or nursing homes, a monitoring system in which various kinds of sensors such as a pressure sensitive sensor are attached around beds has been introduced. However, there is a possibility that contact type sensors may be removed by care recipients who do not like to be monitored. Thus, a system that performs monitoring from a position unreachable by care recipients is desired.

A method for remotely monitoring inside a room using a visible camera is not preferred in terms of protection of privacy of care recipients. Further, in a case where the inside of the room is darkened in a bedtime, sufficient image information cannot be obtained with a visible camera. Thus, as a monitoring method which is capable of night vision and which gives consideration to privacy, a monitoring system using an infrared camera has been proposed.

A system in which an infrared camera is attached right beside a bed and which captures an image of a care recipient from right beside the care recipient has been proposed. This system can detect that the care recipient is sitting up but cannot detect falling or presage of falling from a bed. On the other hand, a system which captures an image of a care recipient from right above, divides a detection range into areas in advance and performs monitoring depending on in which area the care recipient is located has also been proposed (see, for example, PTL 1).

CITATION LIST

Patent Literature

[PTL 1] JP 6828703 B

SUMMARY OF INVENTION

Problem to be Solved by the Invention

In the system that captures an image from right above, a thermal image in a plane of a bed is acquired. However, it is difficult to distinguish between heat of a care recipient and heat remaining on the bed in the thermal image. Thus, whether the care recipient is sitting up in the bed or just turns over in bed cannot be distinguished, and a state of the care recipient cannot be accurately determined.

The present disclosure has been made to solve the problem as described above, and an object thereof is to provide a monitoring system and a monitoring method capable of accurately determining a state of a care recipient.

Solution to Problem

A monitoring system according to the present disclosure includes a thermal image acquisitor attached to a wall or a ceiling on a side of a head of a care recipient in a case where the care recipient lies on a bed, and capturing an image of the bed and its surroundings from diagonally above to acquire a thermal image; reference setting circuitry setting two reference lines respectively corresponding to a left end and a right end of the bed in the thermal image, and a reference height for determining sitting-up of the care recipient: heat source detection circuitry detecting a mass of a heat source in the thermal image: state determination circuitry determining a state of the care recipient from a positional relationship between a safe area enclosed with the reference lines and the reference height and the mass of the heat source; and a determination result output device outputting a determination result of the state determination circuitry.

A monitoring method according to the present disclosure by a thermal image acquisitor attached to a wall or a ceiling on a side of a head of a care recipient in a case where the care recipient lies on a bed, capturing an image of the bed and its surroundings from diagonally above to acquire a thermal image: setting two reference lines respectively corresponding to a left end and a right end of the bed in the thermal image, and a reference height for determining sitting-up of the care recipient, by reference setting circuitry: detecting a mass of a heat source in the thermal image by heat source detection circuitry: determining a state of the care recipient from a positional relationship between a safe area enclosed with the reference lines and the reference height and the mass of the heat source by state determination circuitry: and outputting a determination result of the state determination circuitry by a determination result output device.

Advantageous Effects of Invention

In the present disclosure, an image of the bed and its surroundings is captured from diagonally above to acquire a thermal image, and a state of the care recipient is determined from a positional relationship between the safe area enclosed with the two reference lines and the reference height in the thermal image and the mass of the heat source. By this means, the state of the care recipient can be accurately determined.

DESCRIPTION OF EMBODIMENTS

A monitoring system and a monitoring method according to the embodiments of the present disclosure will be described with reference to the drawings. The same components will be denoted by the same symbols, and the repeated description thereof may be omitted.

First Embodiment

Figure 1:
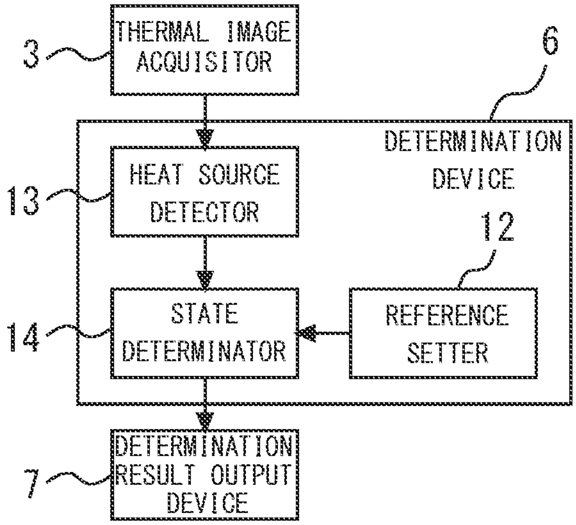
FIG. 1 is a block diagram illustrating a monitoring system according to a first embodiment.
Figure 2:
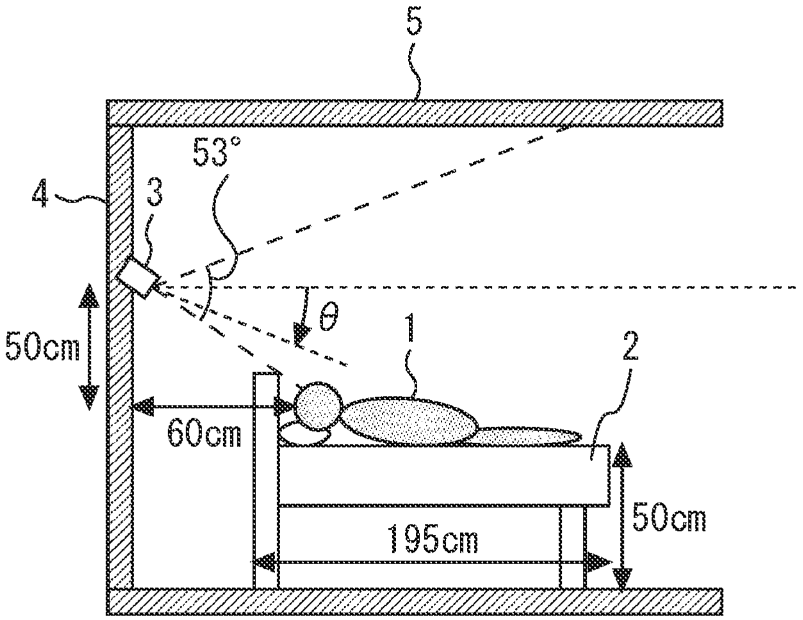
FIG. 2 is a side view illustrating a state where the monitoring system according to the first embodiment is used.
Figure 3:
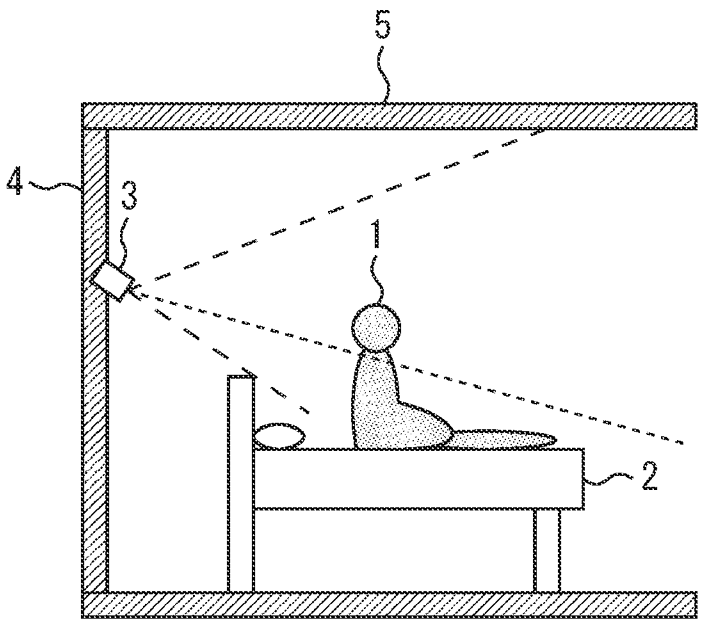
FIG. 3 is a side view illustrating a state where the monitoring system according to the first embodiment is used.
Figure 4:
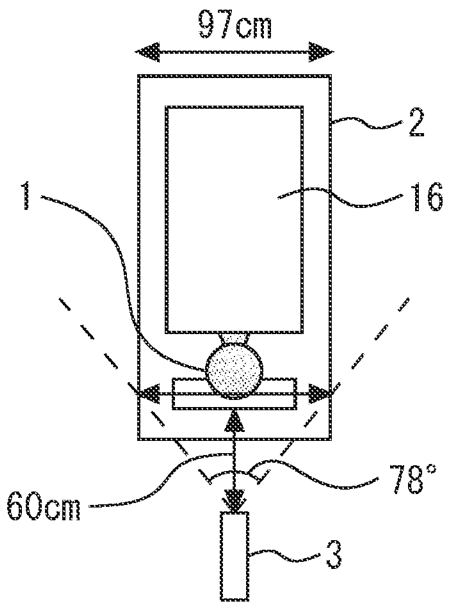
FIG. 4 is a top view illustrating a state where the monitoring system according to the first embodiment is used.

FIG. 1 is a block diagram illustrating a monitoring system according to a first embodiment. FIG. 2 and FIG. 3 are side views illustrating a state where the monitoring system according to the first embodiment is used. FIG. 4 is a top view illustrating a state where the monitoring system according to the first embodiment is used. FIG. 2 and FIG. 4 illustrate a state where a care recipient 1 lies on a bed 2. FIG. 3 illustrates a state where the care recipient 1 is sitting up in the bed 2.

A thermal image acquisitor 3 is attached to a wall 4 on a side of the head of the care recipient 1 in a case where the care recipient 1 lies on the bed 2. However, the thermal image acquisitor 3 may be attached to a ceiling 5. The thermal image acquisitor 3 captures an image of the bed 2 and its surroundings from diagonally above to acquire a thermal image. The thermal image acquisitor 3 is, for example, an infrared array sensor. As the infrared array sensor, for example, a sensor in which infrared sensors such as bolometers, thermopiles and thermal diodes are arranged in a matrix can be used. Use of the infrared array sensor makes it possible to capture an image of the care recipient 1 even within a dark room while giving consideration to privacy.

A determination device 6 analyzes the thermal image acquired by the thermal image acquisitor 3 to determine a state of the care recipient 1. A determination result output device 7, which is, for example, a display, a mobile phone or a tablet terminal that displays the thermal image, outputs a determination result by the determination device 6. Note that the determination result output device 7 may be a speaker, or the like, which notifies a caregiver of the determination result through speech. Information is transmitted from the determination device 6 to the determination device 7 through wireless connection such as Wi-Fi (registered trademark), Bluetooth, 4G or 5G or through wired connection such as a communication cable or a wired LAN.

FIG. 5 to FIG. 10 are views illustrating a thermal image displayed by the determination result output device. In the thermal image, two reference lines 8 and 9 respectively corresponding to a left end and a right end of the bed 2, a reference height 10 for determining sitting-up of the care recipient 1 and a mass 11 of a heat source corresponding to the care recipient 1 are displayed. The thermal image acquisitor 3 captures an image of the bed 2 and its surroundings from diagonally above, and thus, an interval between the two reference lines 8 and 9 becomes narrower from a lower side toward an upper side of the thermal image by perspective. Further, for example, a height of half of the thermal image is set as the reference height 10. The caregiver can know a current state of the care recipient 1 by viewing the thermal image displayed by the determination result output device 7, so that it is possible to reduce a frequency of rushing to the scene due to erroneous determination.

The determination device 6 includes a reference setter 12, a heat source detector 13 and a state determinator 14. The reference setter 12 sets the two reference lines 8 and 9 respectively corresponding to the left end and the right end of the bed 2 in the thermal image, and the reference height 10 for determining sitting-up of the care recipient 1.

The heat source detector 13 detects a region in which a temperature is equal to or higher than a predetermined temperature in the acquired thermal image as the mass 11 of the heat source corresponding to the care recipient 1. The predetermined temperature is a temperature higher than a reference temperature by equal to or greater than a designated temperature. The reference temperature is a temperature of a mechanical shutter incorporated into the infrared camera or a room air temperature and is acquired from the thermal image, a temperature sensor IC attached to the thermal image acquisitor 3, or the like. The designated temperature is arbitrarily set by the caregiver and input upon initial setting. Note that it is preferable to count the number of pixels of the mass 11 of the heat source and exclude a mass whose size does not reach a predetermined minimum size. This can reduce erroneous detection.

The state determinator 14 determines a state of the care recipient 1 from a positional relationship between a safe area 15 enclosed with the reference lines 8 and 9 and the reference height 10 and the mass 11 of the heat source. As will be described below, the state of the care recipient 1 to be determined by the state determinator 14 includes four of "normal", "falling", "warning for falling" and "warning for leaving bed". In a case of "falling", a degree of urgency is high, and thus, a caregiver needs to hastily rush to the scene. On the other hand, in a case of "warning for falling" and "warning for leaving bed", a degree of urgency is low. In this manner, priorities are set for determination results.

Figure 5:
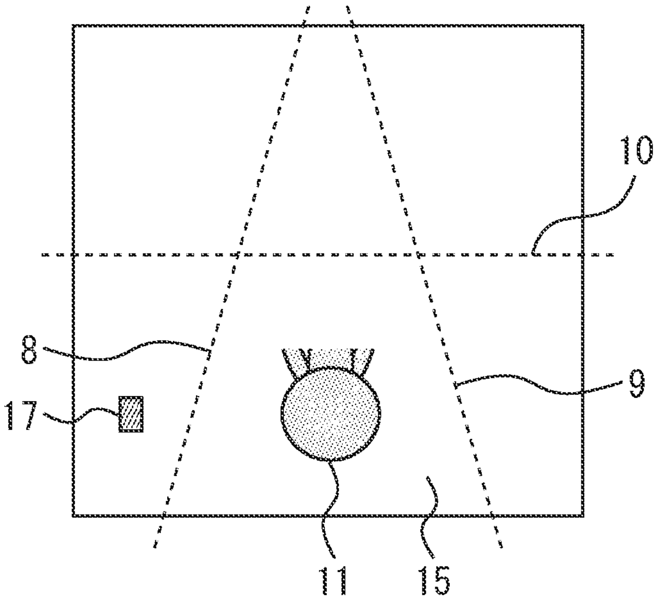
FIG. 5 is a view illustrating a thermal image displayed by the determination result output device.
Figure 6:
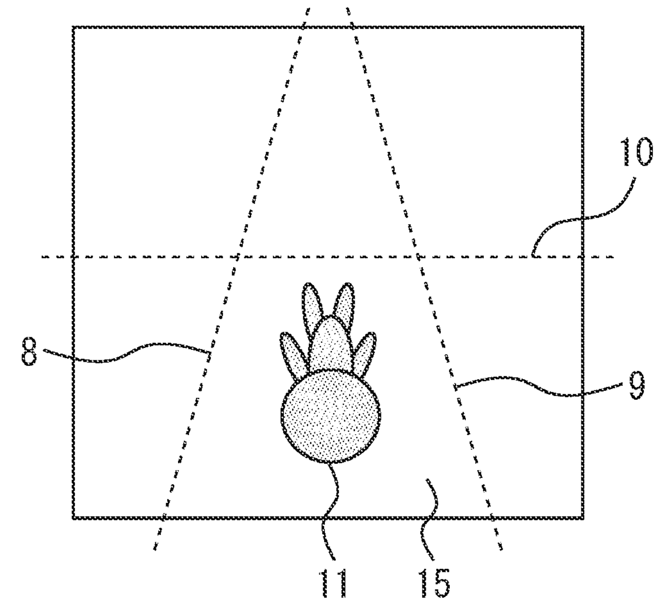
FIG. 6 is a view illustrating a thermal image displayed by the determination result output device.

FIG. 5 and FIG. 6 are thermal images in a state where the care recipient 1 is sleeping. In a case where the care recipient 1 is covered with a blanket 16, as illustrated in FIG. 5, only the mass 11 of the heat source around the head of the care recipient 1 is detected. On the other hand, in a case where the care recipient 1 is not covered with the blanket 16, as illustrated in FIG. 6, the mass 11 of the heat source corresponding to the whole body including the toes of the care recipient 1 is detected. However, a height of the mass 11 of the heat source corresponding to the whole body of the sleeping care recipient 1 is lower than the reference height 10. In the thermal images in FIG. 5 and FIG. 6, the mass 11 of the heat source exists inside the safe area 15, and thus, the state determinator 14 determines that the state of the care recipient 1 is "normal".

In a case where a small heat source such as a smartphone or tea is located within an imaging range, as illustrated in FIG. 5, a plurality of masses 11 and 17 of heat sources are detected in the thermal image. In this case, a maximum one of the plurality of masses 11 and 17 of heat sources is dealt with as the care recipient 1. Thus, the state determinator 14 determines the state of the care recipient 1 from a positional relationship between the maximum mass 11 of the heat source and the safe area 15. Settings may be made in advance so as to remove a small mass 17 of the heat source such as a smartphone. In other words, a size or a temperature of a mass of a heat source to be detected by the heat source detector 13 may be limited within a numerical range of the mass of the heat source corresponding to the care recipient 1.

Figure 7:
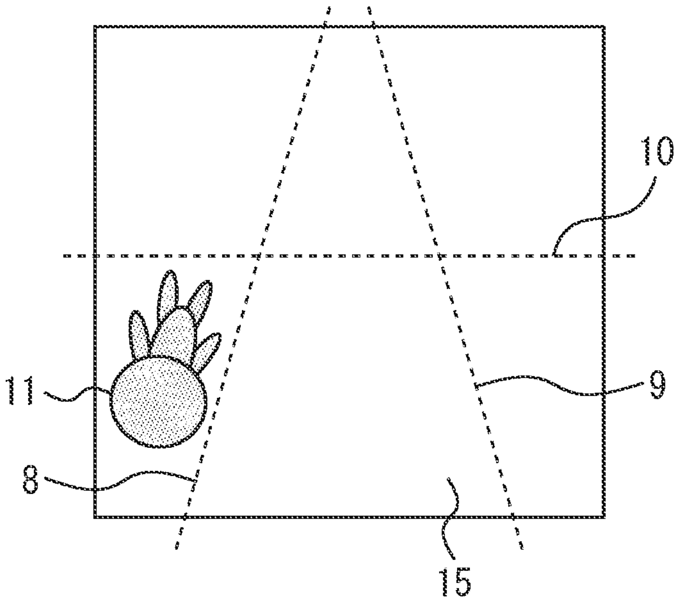
FIG. 7 is a view illustrating a thermal image displayed by the determination result output device.

FIG. 7 is a thermal image in a state where the care recipient 1 falls from the bed 2. If a state where the mass 11 of the heat source is located outside the region between the reference lines 8 and 9 continues for a fixed period, the state determinator 14 determines the state as "falling". The determination result output device 7 notifies the caregiver of "falling" determined by the state determinator 14.

Figure 8:
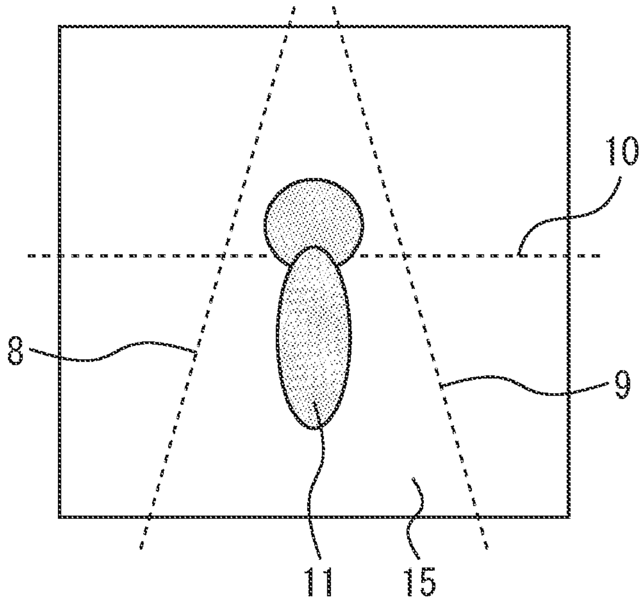
FIG. 8 is a view illustrating a thermal image displayed by the determination result output device.

FIG. 8 is a thermal image in a state where the care recipient 1 is sitting up in the bed 2. A height of part of the mass 11 of the heat source corresponding to the care recipient 1 is higher than the reference height 10. If a state where a height of part of the mass 11 of the heat source is higher than the reference height 10 continues for a fixed period, the state determinator 14 determines the state as "warning for leaving bed" indicating a state where the care recipient 1 is sitting up. The determination result output device 7 notifies the caregiver of "warning for leaving bed" determined by the state determinator 14.

Figure 9:
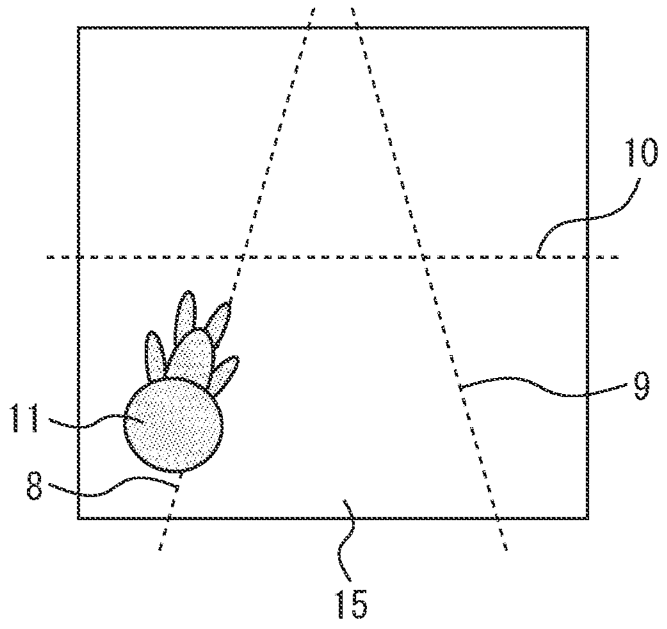
FIG. 9 is a view illustrating a thermal image displayed by the determination result output device.
Figure 10:
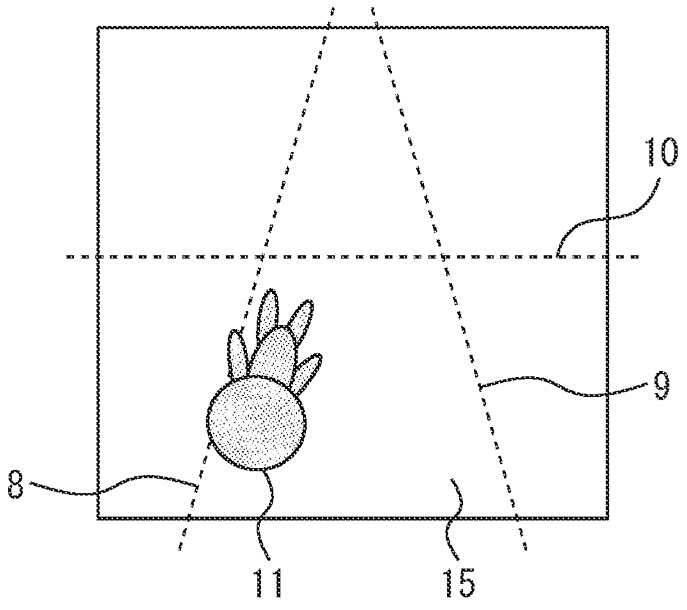
FIG. 10 is a view illustrating a thermal image displayed by the determination result output device.

FIG. 9 and FIG. 10 are thermal images in a state where part of the mass 11 of the heat source corresponding to the care recipient 1 sticks out from the region between the reference lines 8 and 9. In FIG. 9, an area of part sticking out from the region between the reference lines 8 and 9 among the mass 11 of the heat source is equal to or greater than half of the whole area of the mass 11 of the heat source. In this case, the state determinator 14 determines that the care recipient 1 has "fallen". On the other hand, in FIG. 10, the area of the sticking out part is greater than 0 and less than half of the whole area of the mass 11 of the heat source. In this case, the state determinator 14 determines the state as "warning for falling". The determination result output device 7 notifies the caregiver of the determination result by the state determinator 14. In this manner, in a case where a large portion of the mass 11 of the heat source is located outside the region between the reference lines 8 and 9, it is determined as falling so as to enable the caregiver to rush to the scene. On the other hand, in a case where the hand or the foot sticks out from the region, there is a possibility of falling, but the case is not urgent. Thus, in a case where the mass 11 of the heat source slightly sticks out, only attention is called. This can reduce the number of times of rushing to scene due to erroneous determination. Further, by changing notification content in accordance with the degree of urgency, it is possible to reduce load of the caregiver.

Here, there are various ways of attaching the thermal image acquisitor 3 depending on an installation place, and there is a possibility that a position of the bed 2 may move. Thus, the caregiver needs to set the reference lines 8 and 9 and the reference height 10 as necessary. Thus, a method for setting the reference lines 8 and 9 and the reference height 10 will be described.

Figure 11:
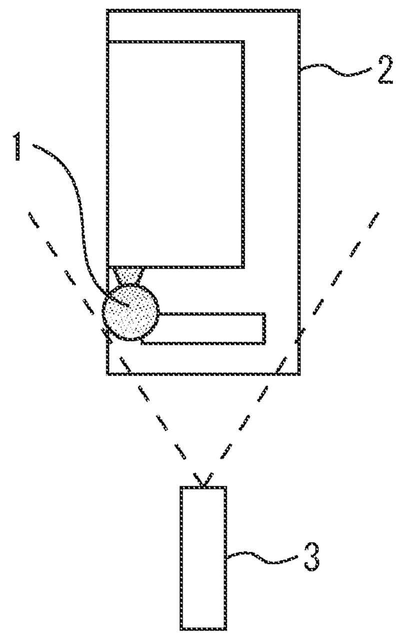
FIG. 11 is a view for explaining a first setting method.
Figure 12:
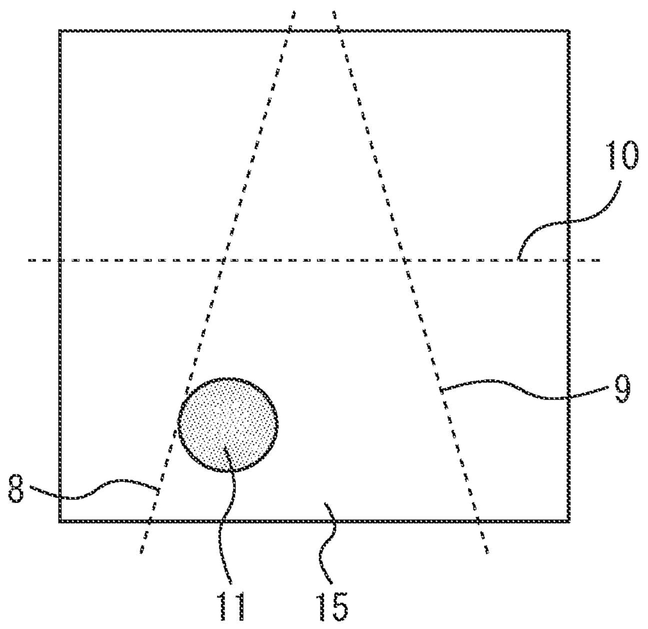
FIG. 12 is a view illustrating a thermal image in which the reference line is set using the first setting method.
Figure 13:
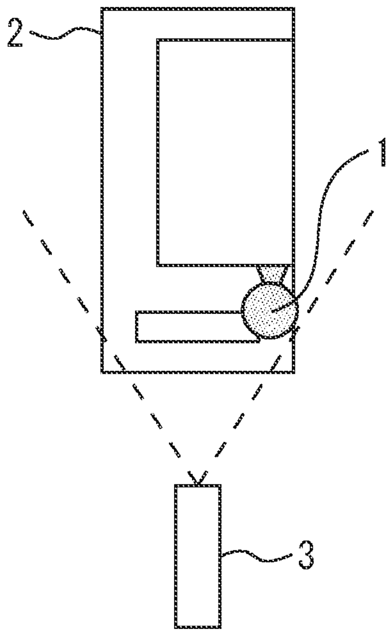
FIG. 13 is a view for explaining a first setting method.
Figure 14:
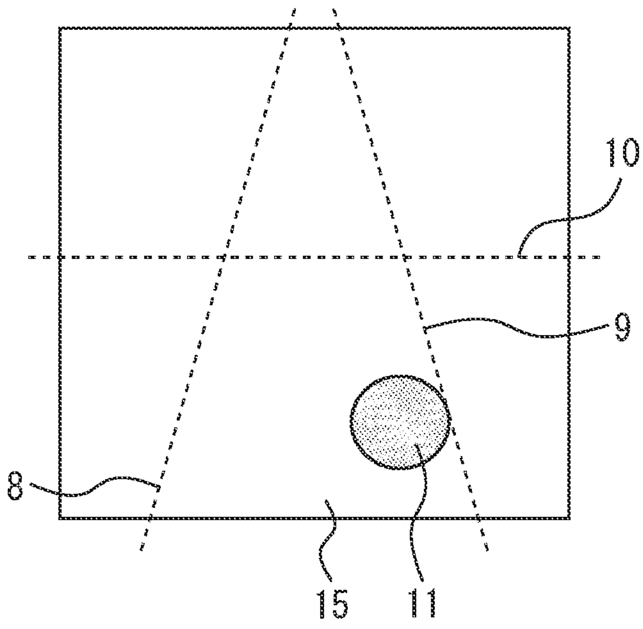
FIG. 14 is a view illustrating a thermal image in which the reference line is set using the first setting method.

FIG. 11 and FIG. 13 are views for explaining a first setting method. FIG. 12 and FIG. 14 are views illustrating thermal images in which the reference lines are set using the first setting method. First, as illustrated in FIG. 11, the care recipient 1 is positioned at a left end of the bed 2, and the thermal image in FIG. 12 is captured. If the caregiver performs remote operation using a PC, a tablet, or the like, to switch a mode of the reference setter 12 to a left end reference line setting mode, the reference setter 12 sets a portion of the left end of the mass 11 of the heat source among the thermal image as the reference line 8 on the left side. In this event, a size of the mass 11 of the heat source which becomes a reference may be also acquired and set. For example, the thermal image acquisitor 3 is set so as to acquire only a mass of a heat source with equal to or larger than a predetermined number of pixels corresponding to a size of a human face.

Then, as illustrated in FIG. 13, the care recipient 1 is positioned on a right end of the bed 2, and the thermal image in FIG. 14 is captured. If the caregiver switches the mode of the reference setter 12 to a right end reference line setting mode, the reference setter 12 sets a portion of a right end of the mass 11 of the heat source among the thermal image as the reference line 9 on the right side. Further, as illustrated in FIG. 3, a thermal image is captured in a state where the care recipient 1 is sitting up in the bed 2. If the caregiver switches the mode of the reference setter 12 to a reference height setting mode, the reference setter 12 sets a head portion of the mass 11 of the heat source among the thermal image as the reference height 10. However, it is necessary to set a position higher than a height of the foot of the mass 11 of the heat source in a state where the care recipient 1 lies on the bed 2 as the reference height 10. By using heat of the human body in this manner, the reference lines 8 and 9 and the reference height 10 can be easily set, so that it is possible to reduce load of the caregiver.

Figure 15:
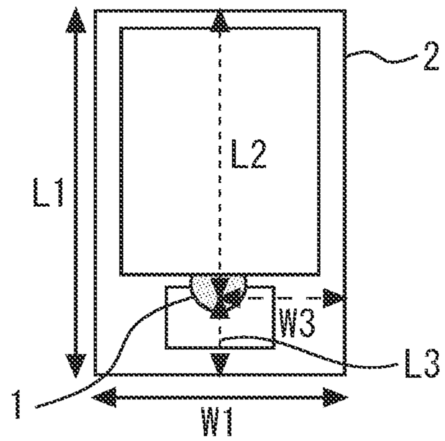
FIG. 15 is a view for explaining a second setting method.

FIG. 15 is a view for explaining a second setting method. A length L1 and a width W1 of the bed 2 are known. In this case, a length L2 of a depth of the bed 2 from a central position of the head of the care recipient 1 who lies at the center of the bed 2, a length L3 to a front side of the bed 2, and a width W3 to the right end of the bed 2 are also known. Upon start of monitoring, the care recipient 1 is made to lie at the center of the bed 2, and a thermal image is captured. A central position of a mass of a heat source corresponding to the head of the care recipient 1 is calculated in this thermal image, and the reference lines 8 and 9 are set from the central position and a known dimension of the bed 2. This enables the reference lines 8 and 9 to be automatically set, so that it is possible to reduce load of the caregiver.

Figure 16:
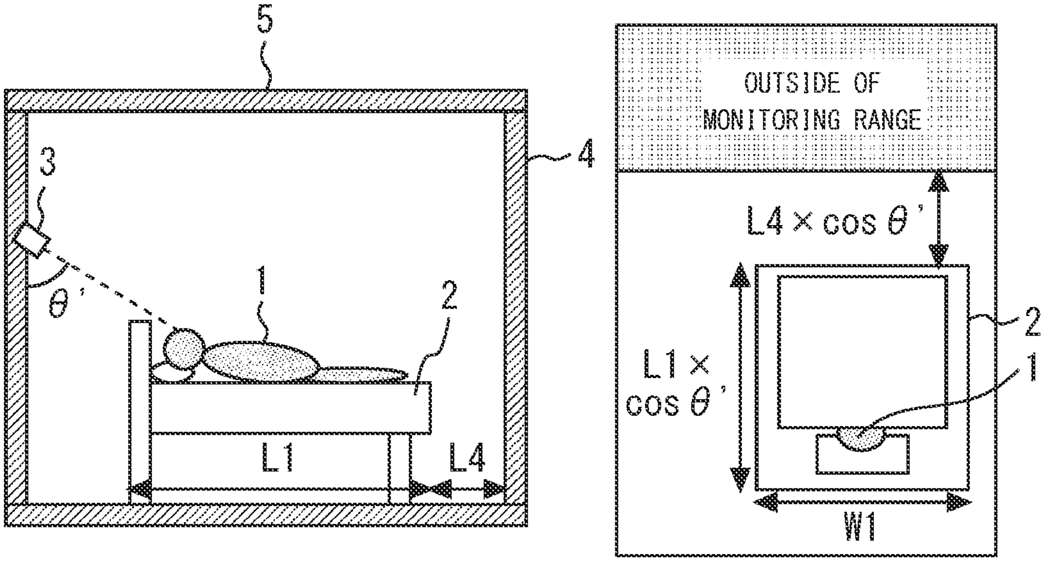
FIG. 16 is a view for explaining a third setting method.

FIG. 16 is a view for explaining a third setting method. The reference setter 12 extracts a region corresponding to a wall 4 in the thermal image from a size (L1×W1) of the bed 2, a distance L4 from the bed 2 to the wall 4 and an imaging angle θ' of the thermal image acquisitor 3. In the thermal image, a length of the bed 2 is L1×cos θ', and a distance from the bed 2 to the wall 4 is L4×cos θ'. The region corresponding to the wall 4 is set as outside of a monitoring range. The state determinator 14 does not use masses of heat sources located outside the monitoring range in state determination. This can reduce erroneous determination by the caregiver being in the image.

As described above, in the present embodiment, an image of the bed 2 and its surroundings is captured from diagonally above to acquire a thermal image, and a state of the care recipient 1 is determined from a positional relationship between the safe area 15 enclosed with the two reference lines 8 and 9 and the reference height 10 in the thermal image and the mass 11 of the heat source. By this means, the state of the care recipient 1 can be accurately determined.

Further, if the care recipient 1 sits up in the bed 2, heat remains in the mattress. Thus, it is difficult to determine whether the care recipient 1 is sitting up or is sleeping if the thermal image is captured from directly above. In contrast, in the present embodiment, the thermal image is captured from diagonally above, and thus, it is possible to discriminate a sitting-up state only from whether a height of the mass 11 of the heat source exceeds the reference height 10 in the thermal image.

Further, in a case where the care recipient 1 is sleeping without being covered with a blanket, the whole body including the toes of the care recipient 1 is detected as the mass 11 of the heat source. Thus, in the present embodiment, the imaging angle of the thermal image acquisitor 3 and the reference height 10 are set so that a height of part of the mass 11 of the heat source corresponding to the care recipient 1 who is sitting up in the bed 2 becomes higher than the reference height 10, and a height of the mass 11 of the heat source corresponding to the whole body including the toes of the care recipient 1 who lies on the bed 2 becomes lower than the reference height 10. This enables determination while distinguishing between a state where the care recipient 1 is sitting up and a state where the care recipient 1 is sleeping without being covered with a blanket.

Specifically, in a case where a height of half of the thermal image is set as the reference height 10, the imaging angle θ of the thermal image acquisitor 3 is set as follows. Here, as the thermal image acquisitor 3, an infrared sensor with a horizontal angle of view of 78° and a vertical angle of view of 53° is used. The bed 2 is assumed to be a single bed having a width of 97 cm, a length of 195 cm, and a height from the floor to an upper surface of the bed 2 of 50 cm. It is assumed that the thermal image acquisitor 3 is attached at a height of 50 cm from the upper surface of the bed 2. In a case where the horizontal angle of view is 78°, it is necessary to separate the thermal image acquisitor 3 from the position of the head by equal to or greater than 60 cm to monitor from the left end to the right end of the bed 2. It is necessary to set the imaging angle θ of the thermal image acquisitor 3 at greater than 13.3° so that the top of the head of the care recipient 1 is at a lower end of the thermal image. On the other hand, it is necessary to set the imaging angle θ of the thermal image acquisitor 3 at smaller than 21.4° so that the toes of the care recipient 1 are located below the reference height 10. Thus, the thermal image acquisitor 3 is set to capture an image of the bed 2 and its surroundings from the angle θ of 13.3° to 21.4° with respect to the upper surface of the bed 2.

Further, in another method for determining the state of the care recipient 1, the thermal image acquisitor 3 periodically acquires a reference thermal image while the care recipient 1 is sleeping. The state determinator 14 stores the reference thermal image and determines the state of the care recipient 1 from a difference between the thermal image acquired during monitoring operation and the reference thermal image. Also with this determination method, the state of the care recipient 1 can be accurately determined.

Second Embodiment

Figure 17:
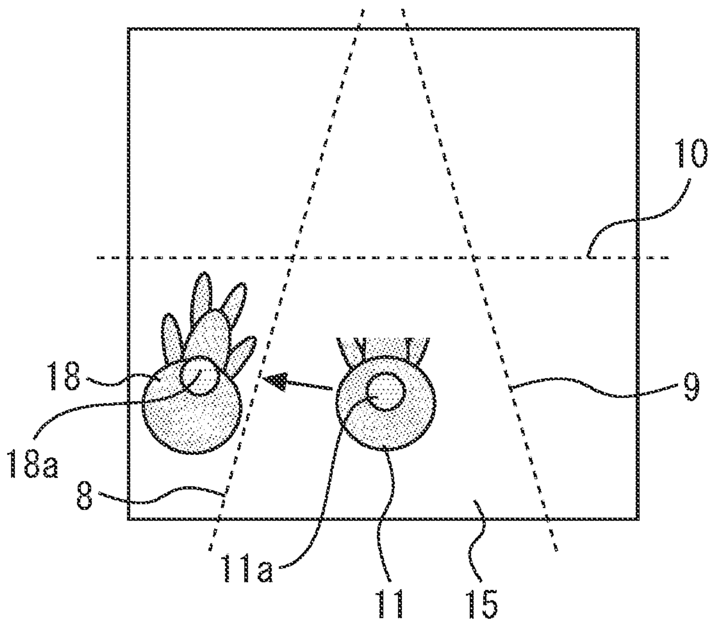
FIG. 17 is a view illustrating a thermal image acquired by a monitoring system according to a second embodiment.
Figure 18:
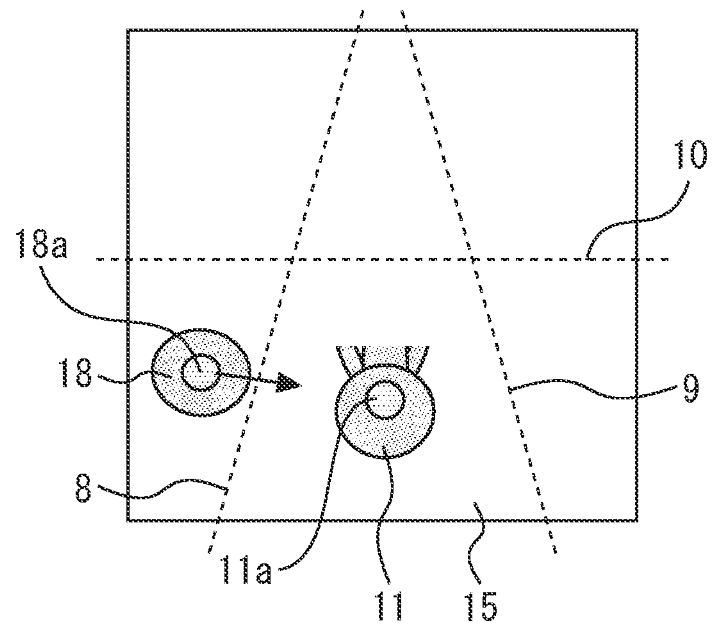
FIG. 18 is a view illustrating a thermal image acquired by a monitoring system according to a second embodiment.

FIG. 17 and FIG. 18 are views illustrating thermal images acquired by a monitoring system according to a second embodiment. In a case where the care recipient 1 has fallen from the bed 2, as illustrated in FIG. 17, a plurality of masses 11 and 18 of heat sources are detected in the thermal image by heat of the care recipient 1 and heat remaining in the bed 2. If the state of the care recipient 1 is only determined with the number of pixels of the mass 11 of the heat source sticking out from the safe area 15, determination cannot be made in a case where a plurality of masses of heat sources exist, and movement of the mass of the heat source cannot be detected.

Thus, in the present embodiment, the state determinator 14 calculates respective central coordinates 11*a* and 18*a* of the plurality of masses 11 and 18 of the heat sources. The state determinator 14 has a function of storing the central coordinates 11*a* and 18*a* in the latest thermal image. Further, in a case where any one of the central coordinates move outside from the region between the reference lines 8 and 9, the state determinator 14 determines the state as a "dangerous state". In a case where the central coordinates move only within the region between the reference lines 8 and 9, the state determinator 14 does not determine the state as the "dangerous state". This can prevent erroneous determination by heat remaining on the bed 2, so that it is possible to improve accuracy of the monitoring system.

Further, in a case where the caregiver approaches the care recipient 1 on the bed 2, as illustrated in FIG. 18, the mass 18 of the heat source corresponding to the caregiver enters the imaging range from outside of the imaging range. The central coordinate 18*a* of the mass 18 of the heat source moves from outside of the region between the reference lines 8 and 9 to inside of the region, and thus, the state is not determined as the dangerous state. In this manner, by detecting how the central coordinates move, the care recipient 1 can be easily distinguished from the caregiver, so that it is possible to prevent erroneous determination by the caregiver being in the image and reduce the number of times of rushing to the scene due to erroneous determination.

Further, in a case where the caregiver is in the room, a monitoring function of the monitoring system is turned off. By this means, it is possible to prevent the state from being erroneously determined as the dangerous state in a case where the caregiver finishes care and moves from inside to outside of the bed 2. After the care is finished, the monitoring function is turned on to start monitoring.

Note that functions of the heat source detector 13, the reference setter 12 and the state determinator 14 may be implemented by recording a program for implementing the functions of the heat source detector 13, the reference setter 12 and the state determinator 14 in a computer-readable recording medium and causing a computer system or a programmable logic device to read the program recorded in the recording medium. Note that the "computer system" described here includes an OS and hardware such as peripheral equipment. Further, the "computer system" includes a WWW system including an environment where a home page is provided (or displayed). Further, the "computer-readable recording medium" refers to a portable medium such as a flexible disk, a magnetooptical disk, a ROM and a CD-ROM, or a recording device such as hard disk incorporated into the computer system. Still further, the "computer-readable recording medium" includes a medium that stores a program for a fixed period, such as a volatile memory (RAM) inside the computer system that becomes a server or a client in a case where the program is transmitted through a network such as the Internet or a communication line such as a telephone line. Further, the above-described program may be transmitted from a computer system that stores the program in a storage device, or the like, to another computer system through a transmission medium or using a transmission carrier in the transmission medium. Here, the "transmission medium" that transmits the program refers to a medium having a function of transmitting information, like a network (communication network) such as the Internet or a communication line (communication wire) such as a telephone line. Further, the above-described program may be a program for implementing part of the functions described above. Still further, the above-described program may be a program capable of implementing the functions described above in combination with a program that has already been recorded in the computer system, that is, a so-called difference file (difference program).

REFERENCE SIGNS LIST

1 care recipient; 2 bed; 3 thermal image acquisitor; 4 wall; 5 ceiling; 7 determination result output device; 8,9 reference line; 10 reference height; 11,17,18 mass of heat source; 11*a*, 18*a* central coordinate; 12 reference setter; 13 heat source detector; 14 state determinator; 15 safe area

The invention claimed is:

1. A monitoring system comprising:

a thermal image acquisitor attached to a wall or a ceiling on a side of a head of a care recipient in a case where the care recipient lies on a bed, and capturing an image of the bed and its surroundings from diagonally above to acquire a thermal image;

reference setting circuitry setting two reference lines respectively corresponding to a left end and a right end of the bed in the thermal image, and a reference height for determining sitting-up of the care recipient;

heat source detection circuitry detecting a mass of a heat source in the thermal image;

state determination circuitry determining a state of the care recipient from a positional relationship between a safe area enclosed with the reference lines and the reference height and the mass of the heat source; and a determination result output device outputting a determination result of the state determination circuitry, wherein if a state where a height of part of the mass of the heat source is higher than the reference height continues for a fixed period, the state determination circuitry determines a state where the care recipient is sitting up, and a height of the mass of the heat source corresponding to whole body including toes of the care recipient who lies on the bed is lower than the reference height.

2. The monitoring system according to claim 1, wherein the thermal image acquisitor captures the image of the bed and its surroundings from an angle of 13.3° to 21.4° with respect to an upper surface of the bed.

3. The monitoring system according to claim 1, wherein an interval between the two reference lines becomes narrower from a lower side toward an upper side of the thermal image by perspective.

4. The monitoring system according to claim 1, wherein if an area of part sticking out from the region between the reference lines among the mass of the heat source is equal to or greater than half of the whole area of the mass of the heat source, the state determination circuitry determines that the care recipient has fallen, and if the area of the sticking out part is greater than 0 and less than half of the whole area of the mass of the heat source, the state determination circuitry determines a state as warning for falling.

5. The monitoring system according to claim 1, wherein if a plurality of the masses of the heat sources are detected in the thermal image, the state determination circuitry determines the state of the care recipient from a positional relationship between maximum one of the plurality of masses of the heat sources and the safe area.

6. The monitoring system according to claim 1, wherein if a plurality of the masses of the heat sources are detected in the thermal image, the state determination circuitry calculates respective central coordinates of the plurality of masses of the heat sources and determines a dangerous state when any one of the central coordinates moves outside from the region between the reference lines.

7. The monitoring system according to claim 1, wherein the thermal image acquisitor periodically acquires a reference thermal image while the care recipient is sleeping, and the state determination circuitry determines the state of the care recipient from a difference between the thermal image and the reference thermal image.

8. A monitoring method comprising:

by a thermal image acquisitor attached to a wall or a ceiling on a side of a head of a care recipient in a case where the care recipient lies on a bed, capturing an image of the bed and its surroundings from diagonally above to acquire a thermal image;

setting two reference lines respectively corresponding to a left end and a right end of the bed in the thermal image, and a reference height for determining sitting-up of the care recipient, by reference setting circuitry;

detecting a mass of a heat source in the thermal image by heat source detection circuitry;

determining a state of the care recipient from a positional relationship between a safe area enclosed with the reference lines and the reference height and the mass of the heat source by state determination circuitry; and outputting a determination result of the state determination circuitry by a determination result output device, wherein if a state where a height of part of the mass of the heat source is higher than the reference height continues for a fixed period, the state determination circuitry determines a state where the care recipient is sitting up.

9. The monitoring method according to claim 8, wherein an imaging angle of the thermal image acquisitor and the reference height are set so that the height of part of the mass of the heat source corresponding to the care recipient who is sitting up in the bed is higher than the reference height, and a height of the mass of the heat source corresponding to the whole body including toes of the care recipient who lies on the bed is lower than the reference height.

10. The monitoring method according to claim 8, wherein the thermal image acquisitor captures the image of the bed and its surroundings from an angle of 13.3° to 21.4° with respect to an upper surface of the bed.

11. The monitoring method according to claim 8, wherein an interval between the two reference lines becomes narrower from a lower side toward an upper side of the thermal image by perspective.

12. The monitoring method according to claim 8, wherein if an area of part sticking out from the region between the reference lines among the mass of the heat source is equal to or greater than half of the whole area of the mass of the heat source, the state determination circuitry determines that the care recipient has fallen, and if the area of the sticking out part is greater than 0 and less than half of the whole area of the mass of the heat source, the state determination circuitry determines a state as warning for falling.

13. The monitoring method according to claim 8, wherein if a plurality of the masses of the heat sources are detected in the thermal image, the state determination circuitry determines the state of the care recipient from a positional relationship between maximum one of the plurality of masses of the heat sources and the safe area.

14. The monitoring method according to claim 8, wherein if a plurality of the masses of the heat sources are detected in the thermal image, the state determination circuitry calculates respective central coordinates of the plurality of masses of the heat sources and determines a dangerous state when any one of the central coordinates moves outside from the region between the reference lines.

15. The monitoring method according to claim 8, wherein the thermal image acquisitor periodically acquires a reference thermal image while the care recipient is sleeping, and the state determination circuitry determines the state of the care recipient from a difference between the thermal image and the reference thermal image.

16. The monitoring method according to claim 8, comprising:

positioning the care recipient at a left end of the bed, capturing a thermal image by the thermal image acquisitor, and setting a portion of a left end of the mass of the heat source among this thermal image as the reference line on a left side by reference setting circuitry; and positioning the care recipient at a right end of the bed, capturing a thermal image by the thermal image acquisitor, and setting a portion of a right end of the mass of the heat source among this thermal image as the reference line on a right side by the reference setting circuitry.

17. The monitoring method according to claim 8, wherein the care recipient is made to lie at the center of the bed, a thermal image is captured by the thermal image acquisitor, and the reference line is set from a central position of a mass of a heat source corresponding to a head of the care recipient in this thermal image and a known dimension of the bed by reference setting circuitry.

18. The monitoring method according to claim 8, wherein the reference setting circuitry extracts a region corresponding to the wall in the thermal image from a size of the bed, a distance from the bed to the wall and an imaging angle of the thermal image acquisitor and sets the region corresponding to the wall as outside of a monitoring range, and the state determination circuitry does not use a mass of a heat source located outside the monitoring range in state determination.

* * * * *